United States Patent [19]

Nappholz et al.

[11] Patent Number: 5,113,869
[45] Date of Patent: May 19, 1992

[54] IMPLANTABLE AMBULATORY ELECTROCARDIOGRAM MONITOR

[75] Inventors: Tibor A. Nappholz, Englewood; William N. Hursta, Littleton; Albert K. Dawson, Denver; Bruce M. Steinhaus, Parker, all of Colo.

[73] Assignee: Telectronics Pacing Systems, Inc., Englewood, Colo.

[21] Appl. No.: 570,379

[22] Filed: Aug. 21, 1990

[51] Int. Cl.⁵ ............................................. A61N 1/05
[52] U.S. Cl. .................................. 128/696; 128/705; 128/903
[58] Field of Search ................ 128/696, 702, 705, 903

[56] References Cited

U.S. PATENT DOCUMENTS

| | | | |
|---|---|---|---|
| 3,212,496 | 10/1965 | Preston | 128/2.06 |
| 3,823,708 | 7/1974 | Lawhorn | 128/2.06 A |
| 3,872,251 | 3/1975 | Auerbach et al. | 179/2 A |
| 4,083,366 | 4/1978 | Gombrich et al. | 128/2.05 T |
| 4,146,029 | 3/1979 | Ellinwood, Jr. | 128/260 |
| 4,223,678 | 9/1980 | Langer et al. | 128/419 D |
| 4,250,888 | 2/1981 | Grosskopf | 128/702 |
| 4,296,756 | 10/1981 | Dunning et al. | 128/716 |
| 4,318,412 | 3/1982 | Stanly et al. | 128/696 |
| 4,702,253 | 10/1987 | Nappholz et al. | 128/419 PG |

FOREIGN PATENT DOCUMENTS

| | | |
|---|---|---|
| 0001708 | 5/1979 | European Pat. Off. |
| 029804 | 1/1987 | European Pat. Off. |
| 2060174 | 4/1981 | United Kingdom |

OTHER PUBLICATIONS

J. D. Meindl et al., "Implantable Telemetry in Biomedical Research;" *IEEE Transactions on Biomedical Engineering*, vol. BME-31, No. 12, Dec. 1984, pp. 817-823.

Primary Examiner—William E. Kamm
Assistant Examiner—Scott M. Getzow
Attorney, Agent, or Firm—Gottlieb, Rackman & Reisman

[57] ABSTRACT

An implanted programmable ambulatory electrocardiography (AECG) patient monitoring device that senses and analyzes electrocardiographic signals from at least one subcutaneous precordial sensor chronically and frequently to detect electrocardiogram and physiological signal characteristics predictive of malignant cardiac arrhythmias. The device includes telemetric capabilities to communicate a warning signal to an external device when such arrhythmias are predicted.

28 Claims, 10 Drawing Sheets

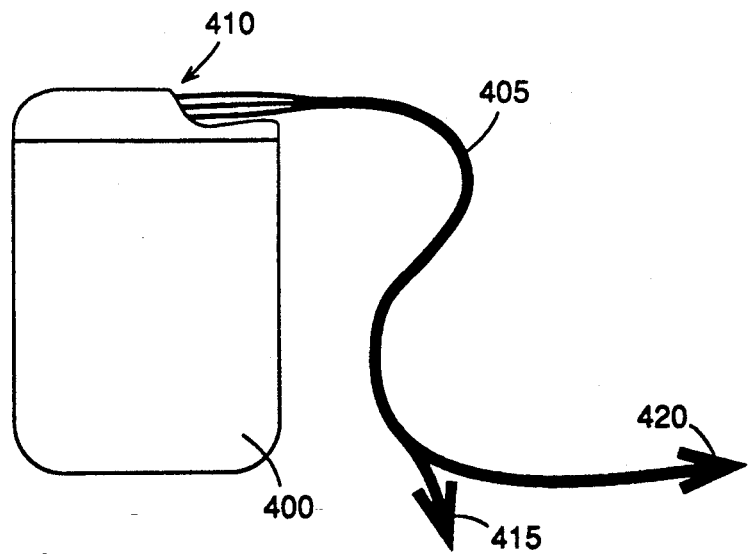
FIG. 8A.
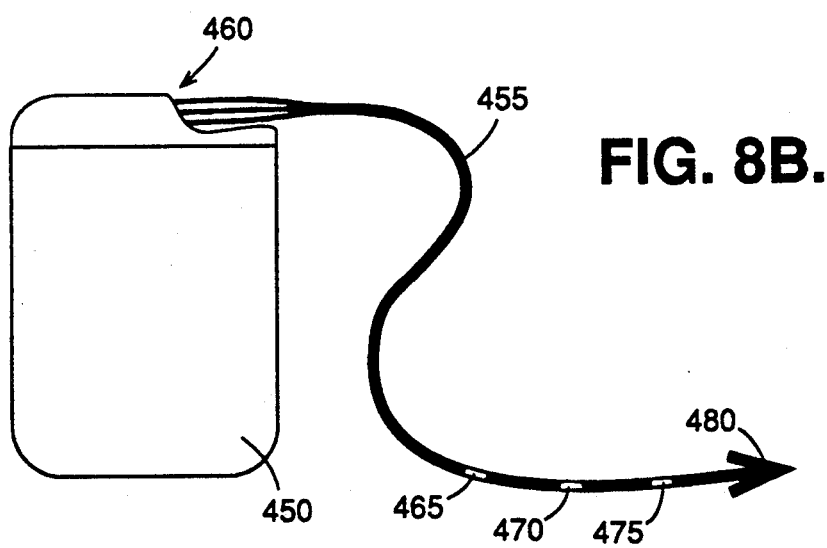
FIG. 8B.
FIG. 13.
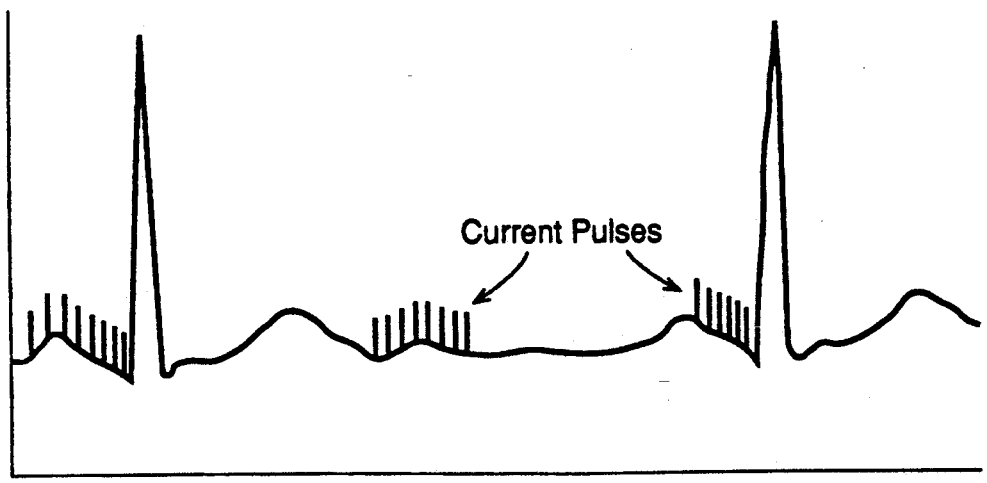

IMPLANTABLE AMBULATORY ELECTROCARDIOGRAM MONITOR

This invention relates to cardiovascular monitoring devices and more particularly to devices performing long-term chronic and frequent monitoring and analysis of cardiac electrical potentials for the purpose of detecting and providing a warning of physiological events premonitory of ventricular fibrillation.

This invention is most closely related to that of prior art ambulatory electrocardiography (AECG) devices which sense and store electrocardiogram (ECG) signals and perform some real-time signal processing, primarily to reduce the amount of stored data. Early AECG systems collected data in full disclosure mode by storing all ECG information recorded within a time period determined by each particular system's storage capacity. Data compression and reduction techniques enable current AECG systems to collect full disclosure mode data for about 24 hours. Medical diagnosis of full disclosure mode data is performed by a medical professional using visual or semi-automatic (computer) analysis.

More recently, real-time analysis AECG systems became available which utilize a microcomputer within the data recorder to implement beat by beat ECG analysis algorithms. Real-time analysis AECG devices normally store information parameters quantifying a diagnostic feature of the ECG signal such as cardiac rate, frequency of ectopic depolarizations, and characteristics of signal morphology during the ST-segment following the QRS-complex. As in the full disclosure mode of operation, test durations last for about one day. But even present-day real-time analysis is not as reliable, in terms of diagnostic specificity and sensitivity, as visual analysis of full disclosure recordings performed by a medical professional. The primary importance of AECG recording is its ability to document transient ECG events that may escape detection during the short recording periods available in the laboratories of hospitals and clinics. These data may then be correlated with other clinical laboratory information to determine diagnoses and treatments.

Prior art AECG systems have allowed clinical researchers to define and detect a number of precursors, antecedent or premonitory signs of malignant cardiac arrhythmias. A clinician performing visual and computer analysis of AECG tape recordings can detect ischemia episodes in patients diagnosed as having coronary artery disease. The presence of ischemia correlates positively with a high risk for the development of ventricular fibrillation or other forms of sudden cardiac death. The frequency and duration of active ischemia episodes characterizes the severity of the risk.

Conventional AECG system components include the AECG recorder, a high speed scanner to replay ECG data, an analyzer to extract diagnostic information from the ECG, and a report generator and printer to tabulate and graph test results. Clinical testing using a conventional AECG system is costly and inconvenient, requiring a good AECG system, a qualified AECG technician to perform a reliable patient preparation and hookup using temporary external leads, and persistence of the patient to maintain an accurate diary of activities performed during the test. An accurate diary allows a physician to distinguish ECG variability and cardiac disease symptoms from physical activity. Behavior modification, the interference with complex individual and social behavior such as emotional state and sleep patterns, results from the inconvenience inherent in AECG monitoring, artificially modifying the data and limiting its usefulness. A clinical test has a limited duration, about 24 hours, after which a physician analyzes the recorded data by transferring the information from the AECG system storage medium (normally reel or cassette tapes) to a display system and later accessing the report generated by the system. Although prior art AECG monitoring enables accurate detection of cardiac arrhythmias (by visual and semi-automatic analysis) and reproduces ST-segment changes for detection and quantification of ischemic heart disease, it can only monitor for a limited time period and requires time-consuming and expensive participation by medical personnel. Time, cost and convenience limitations render prior art AECG systems unable to provide the chronic long-term monitoring and automatic analysis capabilities required for a cardiac emergency warning device.

For a device to chronically and constantly monitor the heart condition and trigger a warning signal in an external communicating device when medical intervention is necessary, it must be continuously reliable. Prior art AECG systems are not sufficiently reliable for long-term monitoring. For example, ST-segment analysis performed using existing AECG systems is limited by mechanical problems and poor signal quality, rendering a high percentage (25 percent or greater) of 24-hour AECG tapes unusable. Electrodes attached externally to the body are a major source of signal quality problems and analysis errors because of susceptibility to interference (muscle noise, power line and high frequency communication equipment interference, and baseline drift from respiration), contact problems, ECG waveform artifacts, and patient discomfort. Externally attached electrodes are subject to motion artifacts from positional changes and the relative displacement between the skin and the electrodes. External electrodes are impractical for long-term recording (longer than 24 hours). One study found that the average useful lifetime of present day external electrodes ranges from 49 to 64 hours before adherence problems, skin irritation, and increasing signal artifacts necessitate electrode replacement.

External electrodes require special skin preparation and care by the patient to prevent signal corruption by dislodgement or wetting from sweating or bathing. Externally attached electrodes lack the signal fidelity required to automatically perform data analysis for automatically identifying sudden death precursors. A cardiac emergency warning device must constantly and reliably detect cardiac events, accurately time these events and analyze details of the waveform morphology. The device must classify the cardiac rhythm as a normal rhythm or an arrhythmia according to the timing and frequency of the cardiac events and measure amplitude and frequency detail within the electrical cardiac waveforms. Externally attached electrodes cannot produce the reliable chronic and long-term data acquisition necessary for the present invention. In prior art AECG recordings, physicians can pick and choose the best cardiac waveforms for visual and semi-automated analysis. A continuously responsive chronically implanted warning device cannot select its signals for analysis. All signals must permit reliable diagnosis.

Limitations inherent in prior art AECG systems prevent their usage for long-term detection and warning of malignant arrhythmias. Traditional AECG systems were intended to perform logging of heart rates and gross ECG features rather than provide for the extensive analysis of cardiac waveforms. Consequently, AECG signal processing capabilities were limited. No known prior art AECG monitors provided analysis for automatically determining a patient's risk of sudden death in the absence of physician intervention. No known prior art monitors initiated communication with an external device to produce a timely warning signal.

One application of AECG signal analysis, the study of ST-segments, illustrates the limitations of prior art AECG monitors. These monitors are designed to measure the coarse features of electrocardiogram waveforms for the purpose of detecting arrhythmias rather than to probe the fine structural detail of portions of the waveforms such as the ST-segment amplitude levels. False-positive and false-negative diagnoses of myocardial ischemia as determined by analysis of ST-segment elevation or depression are common. Inaccuracies begin with inadequate low-frequency response and phase distortion (the nonlinearity in the relationship between the frequency and phase response of the AECG system) of the AECG recorder. Data communication between the various AECG system components magnifies these errors. AECG monitor signals are recorded on tape. Slight errors in the frequency and phase response of the AECG monitor during signal acquisition are accentuated by recording tape distortion which may cause ripple in the frequency response and ECG distortion. AECG systems can attempt to restore electrocardiogram fine detail by performing signal processing but complications arise since the frequency response ripple changes with heart rate. Signal degradation is endemic to external AECG monitoring since a system commonly includes a recorder, a playback system and a printout device, each of which introduces error into the AECG record.

In accordance with the principles of our invention, an AECG monitoring device (the monitor and the leads) is chronically and completely implanted within the body. The device is implanted subcutaneously to sample electrocardiogram signals conveniently, accurately and reliably. The device constantly samples and analyzes the signals to detect precursors of life-threatening malignant arrhythmias and automatically initiates communication with an external communicating device to warn the patient when the results of the analysis call for medical intervention. Leads are positioned such that the full length of a lead, including one or more electrodes, lies beneath the skin with the electrodes located in the precordial region of the chest of the patient. The active electrodes may be located on or near the precordial positions standard in ambulatory electrocardiography. [As used herein, the term "precordial positions" refers to the standard chest positions to which ECG electrodes are attached.] The fact that the electrodes are implanted substantially increases signal accuracy over that of external electrodes in terms of signal to noise ratio, reliability and durability. The device monitors electrocardiographic signals over the long-term (for years), analyzes the signals to detect precursors of malignant arrhythmias and automatically provides a warning message to an external communicating device when the signals indicate the desirability of medical intervention. This method of AECG monitoring in a real-time device capable of long-term monitoring and patient interaction allows early detection of precursors anticipating arrhythmias and intervention to avoid a traumatic cardiac episode. The method of AECG monitoring also detects present cardiac pathology such as myocardial ischemia enabling therapy for prevention of further injury to the heart. This AECG monitoring allows the physician to track the efficacy of oral drug therapy over time to best determine which drugs are effective and in what dosages. Long-term AECG monitoring allows a physician to characterize individuals with regard to ventricular ectopy and ischemia, and to monitor for side effects to drug therapy. At present, physicians have little insight into the effectiveness of drug therapy for a particular patient after the patient leaves the physician's office. Particularly, the physician has very little information about changes in drug effectiveness over time. Only reliable chronic long-term monitoring can provide this important information.

The implantable monitor of the present invention must be able to detect rhythm abnormalities and must also be able to detect repolarization changes in the ECG that may be related to ischemia. The ambulatory recorder and analyzer requires signal acquisition and processing capabilities sufficient to reliably detect precursors, memory to store and analyze information over time, and the communications ability to initiate preventative therapy. It is also desirable, though not necessary, for the device to have the ability to download special purpose signal acquisition and analysis programs to tailor the device to the needs of a particular patient.

Beyond the sensing and analysis of electrocardiograms, the implanted electrodes embodied in this invention are capable of measuring other physiological parameters not normally sensed by traditional AECG systems. The electrodes, or supplemental electrodes across the chest, enable the measurement of electrical impedance (for example, using techniques disclosed in U.S. Pat. No. 4,702,253). From impedance measurements the implanted device can derive respiratory parameters such as respiration rate, tidal volume and minute ventilation. Respiratory parameters reliably reflect patient activity, allowing the monitor to correlate cardiac activity with the influences of physical exertion and psychological stress. The ability to monitor patient activity is important for distinguishing normal cardiac rhythms from arrhythmia. When a patient is exercising, the monitor may set the arrhythmia threshold to a higher heart rate level.

Ultrasound transducers are another sensor type which may attach to the leads and electrically interconnect with the implantable AECG monitor. Using implantable ultrasound transducers, the device can monitor arterial pressure by measuring pressure and flow parameters such as pulse wave velocity within the circulatory system.

The combination of chronic long-term viability and the enhanced accuracy of implantable electrodes extends the device function from the data collection of prior art AECG systems to the control of multiple cardiac devices including defibrillators, antitachycardia pacemakers and drug infusion pumps.

The implantable AECG monitor communicates with multiple components including programmer/analyzer devices, warning alarms, telephonic communicators, data recorders, and defibrillators. Communication allows the external programming device to set control variables to determine the behavior, response, functions and operations performed by the implantable monitor. The external programming device may download control programs into the implantable device memory to tailor its execution for the desired cardiac therapy.

A primary difference between prior art AECG monitoring systems and the present invention is that the present invention is an implantable AECG monitoring device. This implantable form completely changes the nature of AECG monitoring in three ways: long-term and constant monitoring is practical only in an implantable system, implanted electrodes substantially increase system accuracy, and information is not altered by behavior modification. For an AECG monitoring device to be beneficial to a patient with coronary artery disease, angina or who otherwise suffers from silent myocardial ischemia it must monitor cardiac signals constantly, in real time, and for the long-term. Some important diagnostic events occur only very rarely. An external AECG system, collecting data for only about 24 hours per session, is unlikely to detect these events while an implantable system with constant long-term monitoring will. Some changes in cardiac function take place very slowly over time, sometimes over a period of weeks or months. Monitoring for only a few hours or days will fail to detect these changes. A basic premise of this invention is that only an implanted device can conveniently monitor in a chronic long-term manner with constant and frequent signal sampling and precursor analysis to safely provide an early warning of potentially fatal conditions. AECG monitoring, as well as electrophysiology and stress testing, attempt to measure cardiac response in a real-life setting. Only an implantable device can truly sense real-life phenomena. An implantable device requires implantation and calibration only once, producing stable information for the lifetime of the device. Only an implanted device can acquire electrocardiographic signals with sufficient quality and reliability to effectively detect these precursors. Only information from an implanted system will detect all significant cardiac events, avoid artifacts or errors caused by behavior modification and track over the long-term without signal deterioration.

Because implantation is critical to its functionality the present invention must be distinguished from another chronically implanted device, the cardiac pacemaker. Like the present invention, prior art cardiac pacemakers include the basic components of an implantable AECG monitor: leads for sensing electrical cardiac activity, memory storage and signal processing capabilities for analyzing the electrical activity, and communication circuits for communicating with an external device.

A primary difference between the implanted AECG monitoring device and a cardiac pacemaker is the contrast in the functions performed by the devices. The implanted AECG monitoring system measures electrocardiographic signals over the long-term, analyzes the signals to detect precursors of malignant arrhythmias, and automatically triggers a warning signal in an external communicating device when the ECG signals call for medical intervention. Fundamentally, a cardiac pacemaker generates electrical activity for stimulating the heart using electrodes attached to cardiac tissue within the heart. The pacemaker uses a common electrode and lead system both to generate stimulating pulses and to sense the natural electrical activity for inhibiting pacing stimulation. The pacemaker only secondarily uses the electrode and lead system to sample and analyze intracardiac electrical potential information. The pacemaker may use the sensed intracardiac information for analysis in a manner similar to that performed by the AECG monitoring device but it would do so at the expense of the energy required for pacing. Limiting energy expenditure is important in an implanted device. No prior art pacemakers constantly monitor intracardiac waveforms. No prior art pacemakers analyze AECG signals in the manner of the present invention. Nor do any pacemakers function as a precursor warning device.

The implanted AECG monitoring device does not stimulate the heart. It is incapable of pacing the heart since there is no means for delivering pacing stimulation voltage pulses nor electrodes implanted in the heart. Because the AECG monitor does not expend any energy to pace the heart it may perform different functions including more complex signal processing and analysis or it may have an extended lifetime as compared to a pacemaker. An implanted AECG monitoring device and a pacemaker have different circuitry resources devoted to signal storage and processing. Because resources in an implanted device are conserved to minimize energy drain, a dedicated AECG monitoring device with no pacing capability can be provided with additional memory and signal processing components to allow long-term storage and ECG data analysis. While the field of the present invention may include that of pacing, the invention would not have been possible (using current technology) without the inventors, all pacemaker designers, having realized that while the device must have many attributes of a pacemaker, one—the main one, pacing—must be omitted.

The location of the implanted leads and electrodes are different in a pacemaker and the implanted AECG monitoring device. The implanted AECG monitoring system uses subcutaneous precordial implantation of the electrodes. The electrodes are implanted subcutaneously in the fatty tissue beneath the dermis but above muscle fascia, positioned on or near any of the precordial positions customary in external ECG monitoring. Implantation in this manner involves minimal surgical invasion and no invasion of the heart. The electrodes of a cardiac pacemaker are implanted within the heart, requiring surgical invasion into myocardial tissue. A physician positions cardiac pacemaker electrodes within the heart for the purpose of stimulating cardiac tissue. In pacing, an important consideration is to implant the lead or leads to minimize the threshold voltage required to stimulate the heart. Positioning the leads in this manner does not guarantee the sensing of an intracardiac signal which will allow the detailed signal analysis required for cardiac arrhythmia precursor detection. A pacemaker's intracardiac signals have an amplitude and morphology highly dependent on the location of leads within the heart and the locally variable capability of cardiac tissue to polarize. Intracardiac signals may contain none of the information necessary for anticipating malignant cardiac rhythms. For example, a myocardial infarction may render the intracardiac signal useless for detecting arrhythmia precursors. A physician would be very unlikely to implant leads in the myocardium in a location which would compromise pacing and raise the pacing threshold just to maximize the signal processing capabilities for arrhythmia detection.

The signals analyzed by the implanted AECG monitoring device are more similar to external electrocardiograms than intracardiograms. In fact, a physician is likely to position the implanted leads of the AECG system to correspond to one of the precordial positions standard in electrocardiography. In contrast, cardiac pacemakers sense intracardiograms which are not standardized according to the classical lead positions known in electrocardiography. This difference is important because the research in ECG analysis for identifying arrhythmia precursors is based on standard lead positioning. Analysis of arrhythmia precursors using intracardiograms would require an entirely new data base. Our invention allows standard, well-developed, analytical techniques to be used, thus saving perhaps years of design time.

While both the internal AECG monitor and the pacemaker communicate with external devices over a communication link, the AECG monitor is intended to initiate communication to a dedicated external communicator and send warning messages to the communicator to begin medical intervention. The external communicator should always be accessible to the implant. No known prior art pacemakers initiate communication but rather respond to requests of the external device. The implanted AECG device provides for the capability of communicating with multiple and different external devices. These devices can warn the patient of dangerous conditions or alert the patient's physician over standard telephone lines.

Further objects, features and advantages of our invention will become apparent upon consideration of the following detailed description in conjunction with the drawings, in which:

FIGS. 8A-8B illustrates the implantable electrocardiogram monitor in its operative condition, showing various elements and attachments including a lead with dual tined electrodes (FIG. 8A) and a lead with a single tined electrode on its distal tip and multiple ring electrodes (FIG. 8B);

Figure 14:
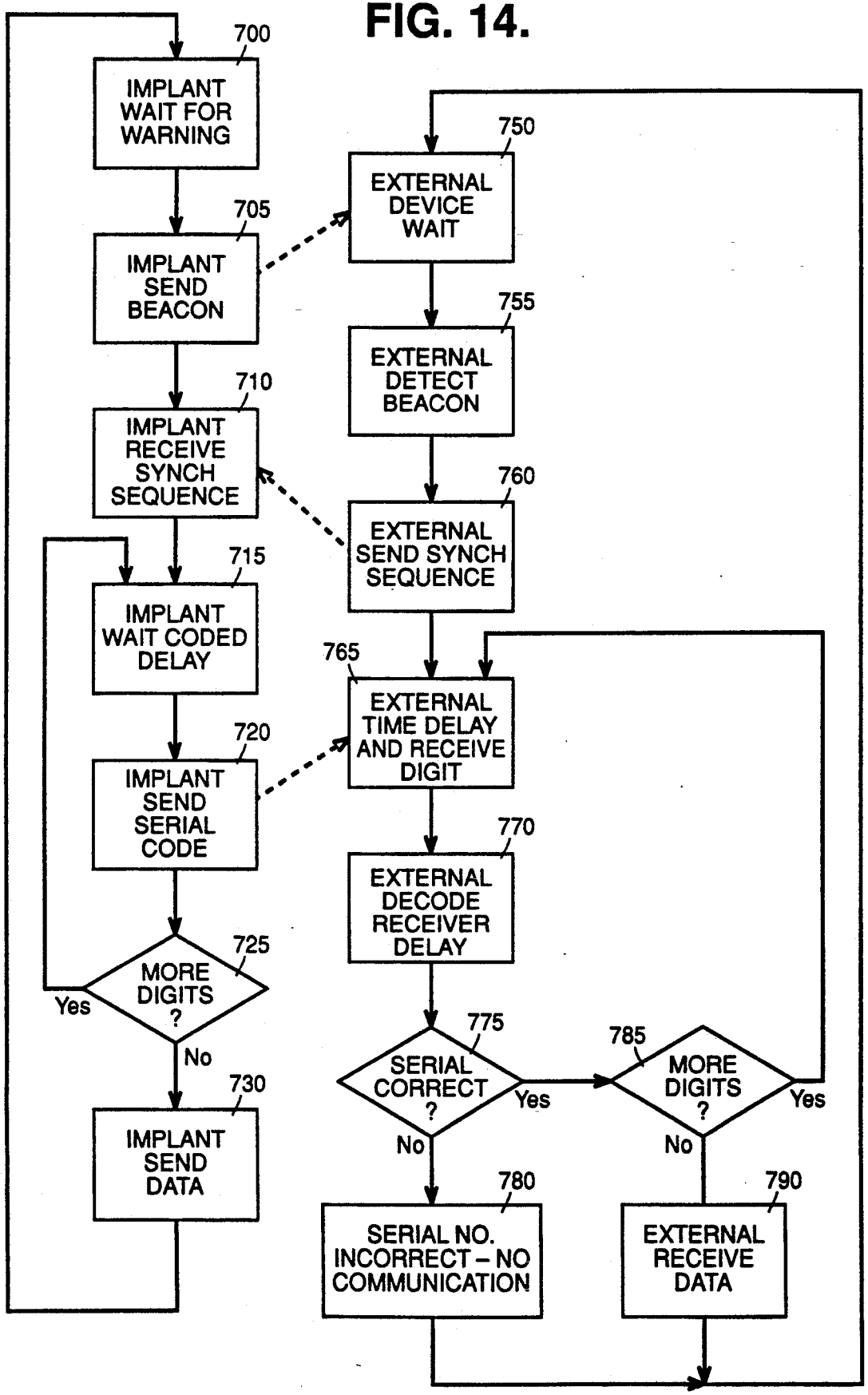

FIG. 13 is a sample electrocardiogram illustrating the method of conductive communication from an external defibrillator which injects low amplitude current pulses into the body which superimpose upon the ECG signal for detection by the implantable AECG monitor; and FIG. 14 is a flow chart illustrating the method by which the implanted AECG monitor establishes communication with an external device programmed to interact with the particular monitor.

Figure 1A:
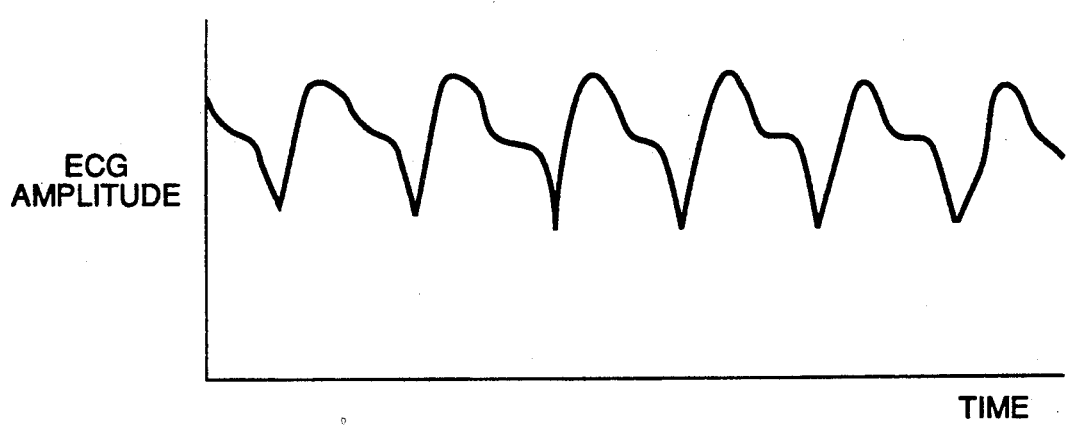
FIGS. 1A-1C is an illustration of sample electrocardiograms (ECGs) showing abnormal cardiac rhythms recognized as precursors to malignant cardiac arrhythmias detected by the implantable AECG monitor, including ventricular tachycardia (FIG. 1A), ventricular couplets (FIG. 1B) and premature ventricular complexes (FIG. 1C)
Figure 1B:
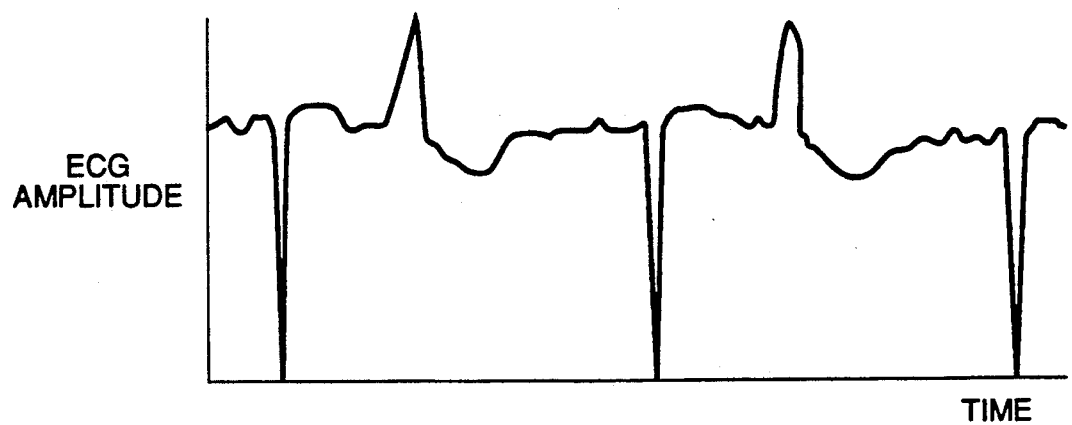
Figure 1C:
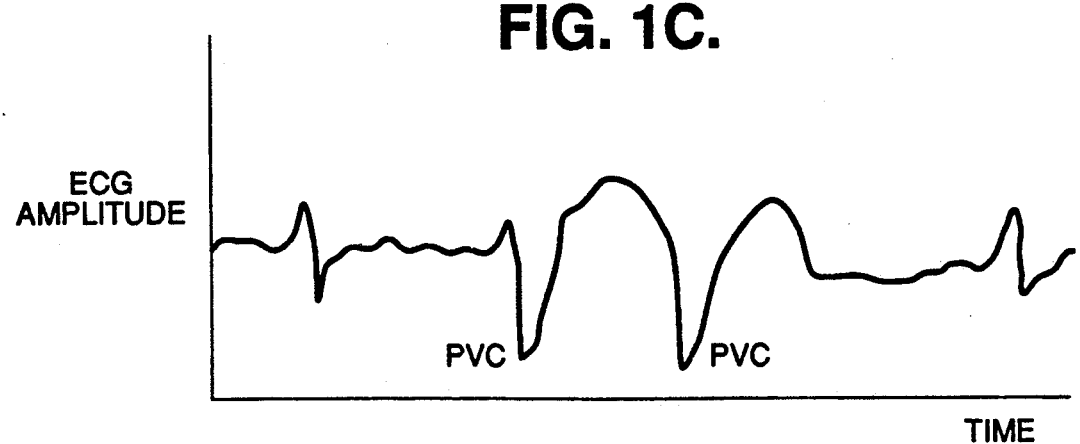

Some AECG features are common in patients experiencing potentially lethal ventricular tachyarrhythmias. Two types of precursors have been identified which are antecedent to ventricular fibrillation or sudden death relating to: (a) abnormal ventricular rhythms, and (b) abnormal electrocardiogram polarization waveforms. FIG. 1 illustrates ventricular fibrillation precursors displaying abnormal ventricular rhythms in the form of complex ventricular arrhythmias including ventricular tachycardia (FIG. 1A), ventricular couplets (FIG. 1B) and premature ventricular complexes or PVCs (FIG. 1C). The level of complexity of such ventricular arrhythmias (for example, dynamic oscillations in the rate of emergence of ventricular tachycardia or wild variations in the length of ventricular tachycardia outbursts) and an increasing rate of occurrence of ventricular arrhythmias are as important as the presence of such arrhythmias in the detection of precursors. The density of ventricular arrhythmias (the ratio of abnormal to normal ventricular rhythms) is also helpful for diagnosing harmful arrhythmias.

Figure 2A:
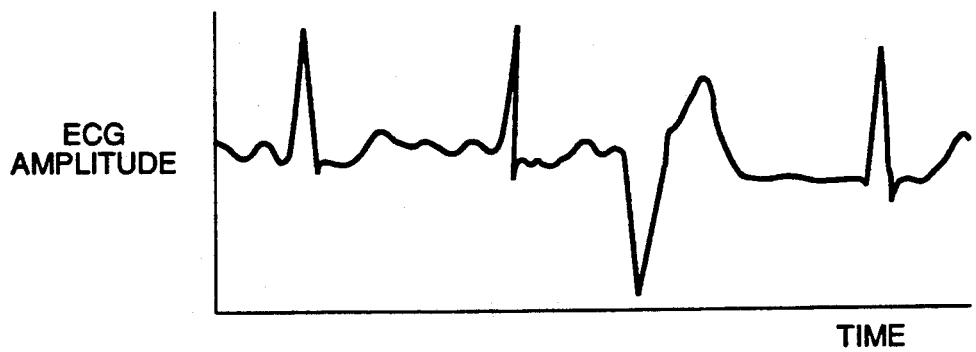
FIGS. 2A-2B is an illustration of samples of the detailed morphology of ECGs recognized as precursors to malignant cardiac arrhythmias detected by the implantable AECG monitor, including premature ventricular depolarizations (FIG. 2A) and repolarization abnormalities such as a long QT interval (FIG. 2B)
Figure 2B:
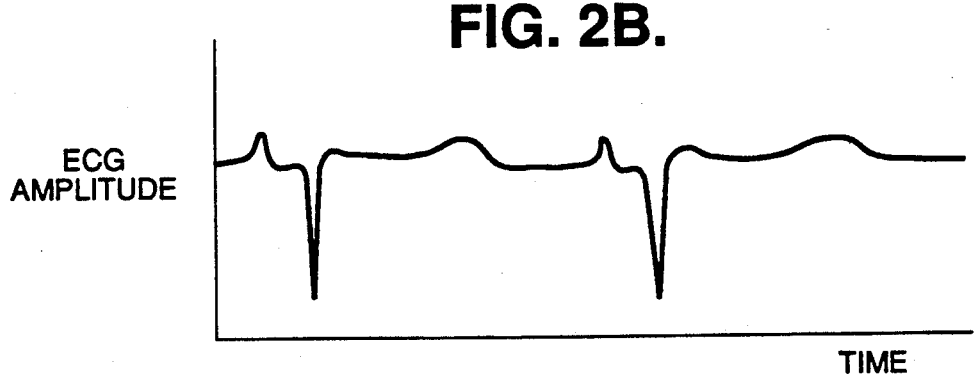
Figure 3A:
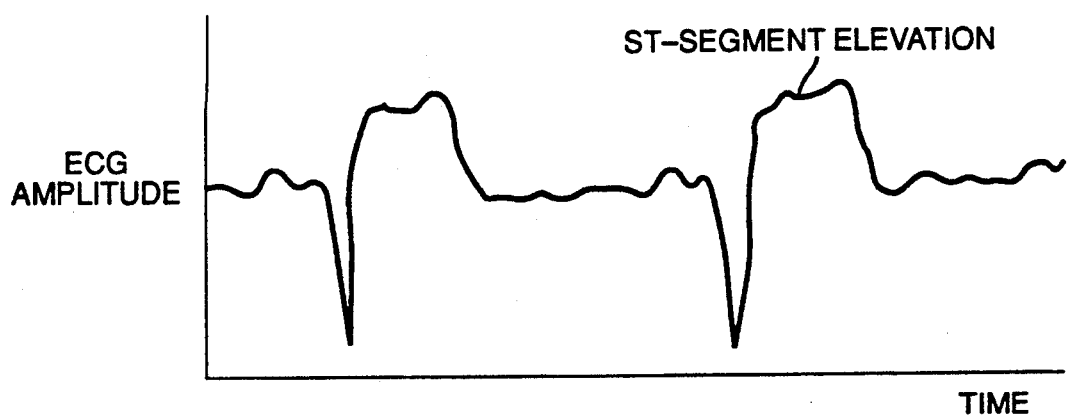
FIG. 3A-3C is an illustration of samples of the detailed morphology of ECGs recognized as precursors to malignant cardiac arrhythmias detected by the implantable electrocardiogram monitor, including ST-segment elevation (FIG. 3A), ST-segment depression (FIG. 3B) and late potentials (FIG. 3C)
Figure 3B:
Figure 3C:
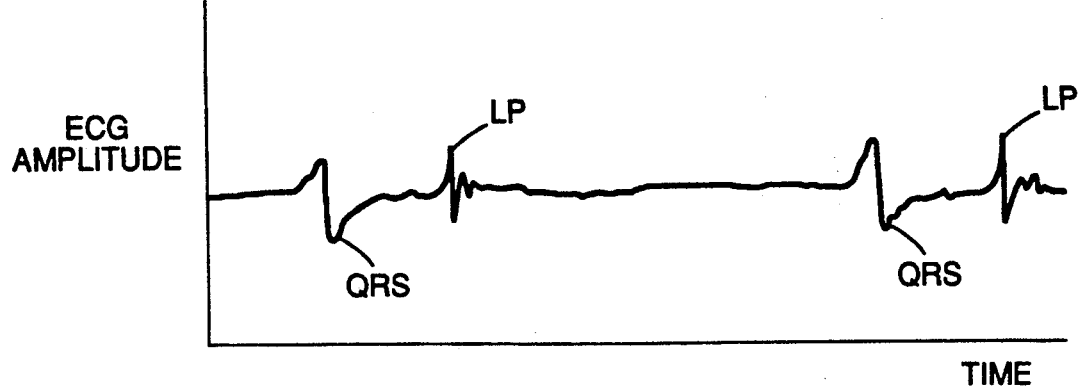

Precursors characterized primarily by abnormalities in the electrocardiogram waveform rather than by abnormalities in cardiac rhythm include repolarization abnormalities, ST-segment changes and late potentials. Detecting waveform abnormality precursors requires the AECG device to analyze the fine detail within ECG waveforms. The implanted AECG monitor analyzes the fine detail of ECGs to detect R-on-T ventricular premature depolarizations (FIG. 2A) which frequently initiate a malignant arrhythmia, repolarization abnormalities such as a prolonged QT intervals (FIG. 2B), and ST-segment changes (FIGS. 3A and 3B, ST-segment elevation and depression). All have diagnostic significance in predicting imminent ventricular fibrillation. Late potentials (designated LP in FIG. 3C) also anticipate episodes of ventricular tachycardia or fibrillation.

The timing of particular precursors, as well as their presence, is diagnostically important for determining the onset and risk of sudden death. In many cases, the maximum incidence of intermediately frequent (from 100 to 500 per hour) premature ventricular complexes occurs between fifteen and six hours prior to ventricular fibrillation. This is followed by an increased frequency in ventricular couplets and runs of complex ventricular arrhythmias including ventricular tachycardia. Repolarization abnormalities often appear in the ECG waveform several hours before ventricular fibrillation. Often there is an increased incidence of ST-segment changes of amplitude greater than 2 mm throughout the risk period and lasting until the third hour prior to sudden death when ST-segment changes of this amplitude diminish in incidence. Over the final six hours preceding sudden death there is an increased incidence of lower amplitude ST-segment changes, usually in the direction of elevation. During these final hours the ST-segment change gradually diminishes from a high amplitude toward the baseline.

Figure 4:
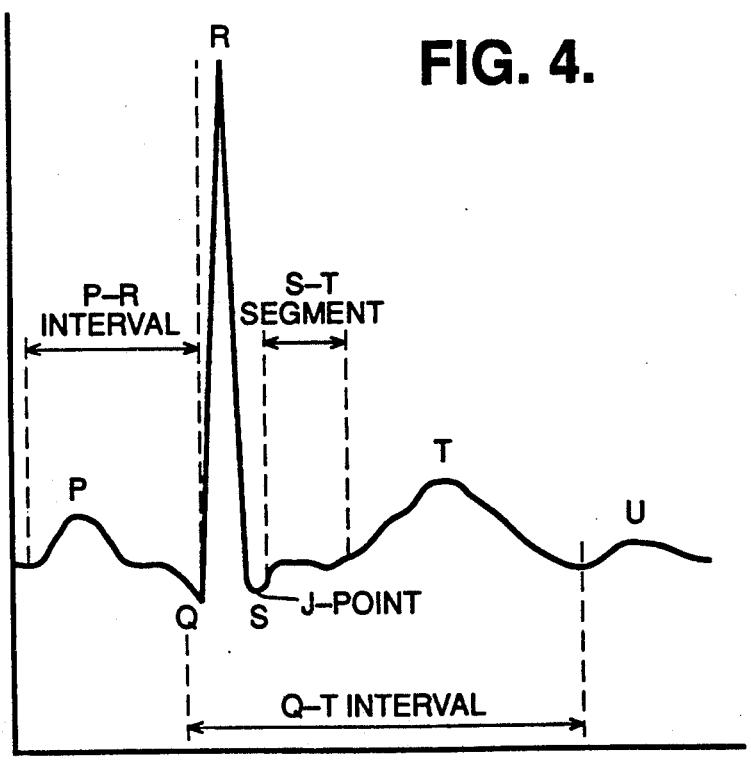
FIG. 4 is an illustration of a normal electrocardiogram (ECG) signal.

The implantable AECG monitor constantly acquires electrocardiogram signals. From these signal waveforms the monitor detects ventricular events and analyzes the fine detail of portions of the signal using known analytical techniques. (As described above, this is possible because prior art pacing leads, with electrodes in and near the heart, are not used while prior art external electrode positions, remote from the heart, are preferably employed.) Much of the diagnostic detail of an electrocardiogram lies in the vicinity of the QRS-complex. FIG. 4 illustrates the waveform of a normal cardiac cycle together with the conventional timing intervals. [ST and QT-intervals end, respectively, at the beginning and end of the T-wave.] Normal P waves have a duration of from 0.04 to 0.08 seconds and precede the R wave (the P-R interval) by from 0.12 to 0.20 seconds. The QRS-complex, which begins with the Q wave and ends with the S-wave, normally has a duration of 0.04 to 0.10 seconds.

Figure 5:
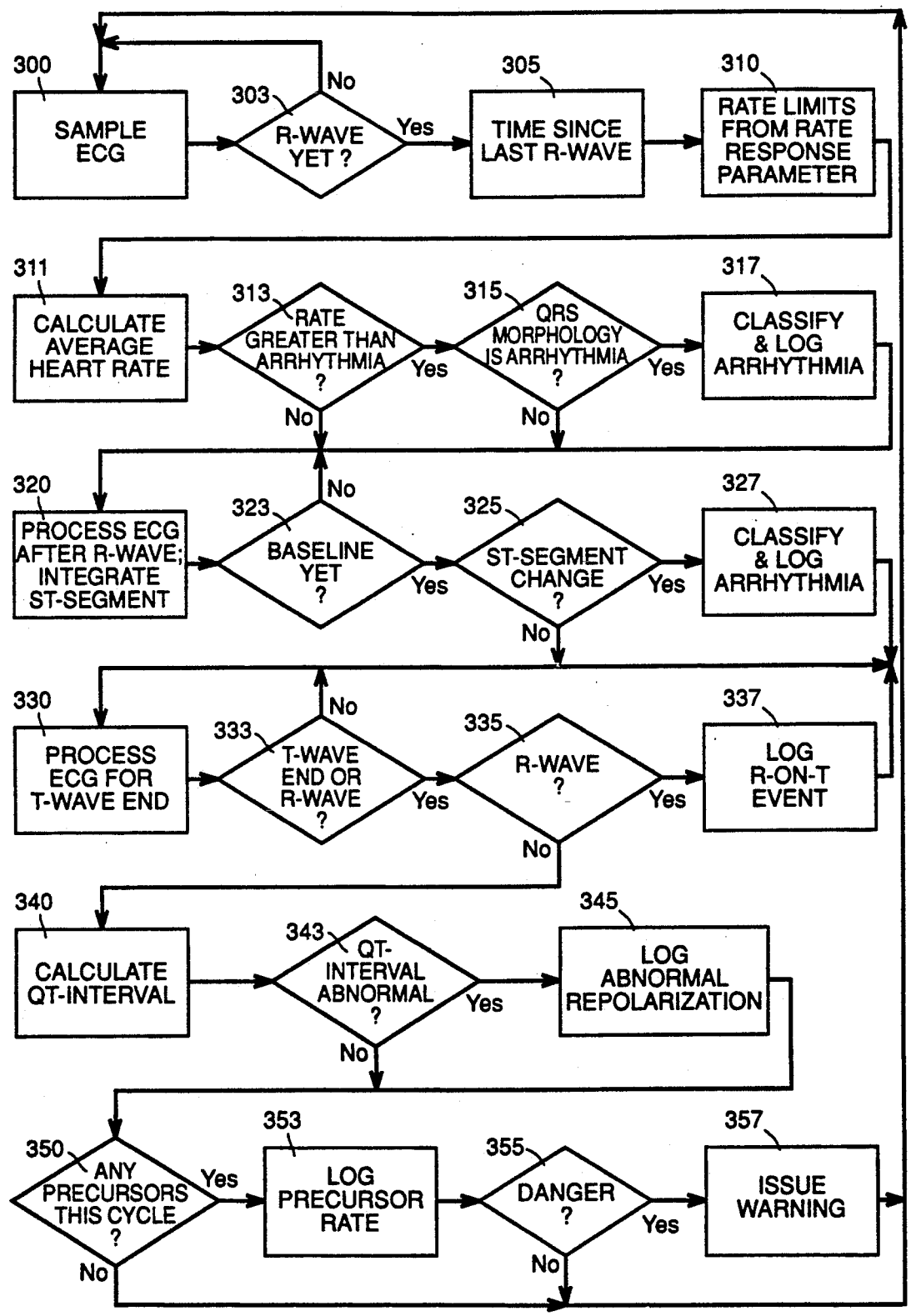
FIG. 5 is a flow diagram illustrating the method performed by the implantable electrocardiogram monitor for detecting precursors of malignant cardiac arrhythmias and transmitting warning messages to an external device.

For each cardiac cycle, the monitor performs the operations shown in the flow diagram of FIG. 5. Generally, the AECG device identifies cardiac events, correlates the events with time intervals within the cardiac cycle, and analyzes the detailed structure within the electrocardiogram. While sensing electrocardiogram signals the AECG monitor first searches for the R wave within the present cardiac cycle in block 303. The R wave normally has the largest slope within the cardiac cycle (the greatest change in polarization amplitude in a short time) and a large amplitude. The preferred embodiment of the invention uses a delta comparator, a slope detector, to detect the R wave. The monitor continuously samples in block 300 until it detects an R wave in block 303. As part of the sampling process in block 300, the monitor saves data relating to morphology of the QRS-complex for further analysis. This data may include samples of ECG amplitude, maximum positive and negative polarity excursions and derivatives (slopes) of the leading and trailing edge of the QRS-complex. After detecting the R wave the AECG monitor determines the elapsed time since the last R wave in block 305. The reciprocal of the elapsed time is the instantaneous heart rate for the present cycle. The monitor calculates this reciprocal value and averages the instantaneous rate over a few cardiac cycles (for example, four) to determine the average rate in block 310. The monitor may average either interval samples or rate samples when determining the average rate. In block 313 the monitor compares the current average rate to predetermined limit values. These limits reflect the rates of various types of arrhythmias. The limits may vary, depending on certain physiological characteristics, indicative of exercise, for example. Standard rate-responsive sensors may be used for this purpose. Therefore, before the test in block 313, the rate limits are set in block 311 in accordance with whichever standard rate-response parameter is monitored.

For example, the monitor may measure impedance signals from the electrodes and convert the impedance signals to a metabolic indicator heart rate, a rate consistent with the physical exertion level of the patient in the manner disclosed in U.S. Pat. No. 4,702,253. The monitor may use the metabolic indicator heart rate to determine the boundaries between normal exercise rhythms and arrhythmias in block 311. In this regard, reference may be made to U.S. patent application Ser. No. 497,002, entitled "A METABOLIC DEMAND DRIVEN RATE-RESPONSIVE PACEMAKER", filed on Mar. 20, 1990, in the names of Tibor A. Nappholz, et al, which application is hereby incorporated by reference. In addition to the magnitude of the heart rate, the monitor may detect variability or stability in heart rate over time to classify cardiac rhythms for characterizing susceptibility to sudden death.

If the average rate lies within the boundaries set for a particular class of ventricular arrhythmia in block 313, the monitor (in block 315) tests the morphology of details within the QRS-complex against predetermined and stored morphology parameters to classify the rhythm as either an arrhythmia or a normal rhythm. If the monitor detects an arrhythmia, it classifies the arrhythmia according to type and logs the occurrence of the particular arrhythmia type in memory in block 317.

The preferred embodiment of the invention performs data logging by entering a code designating the arrhythmia type in a circular buffer, a means for storing a history of events in a manner so that oldest events are replaced by the most recent events. Each memory position in the circular buffer denotes a point in time; therefore, the index into the circular buffer points to arrhythmia type/time of day pairs of data.

In block 320 the monitor processes subsequent samples and analyzes the ECG signal from the R wave to the T wave to determine the QT interval and to diagnose myocardial ischemia from ST-segment morphology. The ST-segment occurs in the sampling window beginning at the J-point following a QRS-complex as is known in the art (see FIG. 4) and persists for at least 80 milliseconds. ST-segment depression, defined as a horizontal or downsloping shift of 0.1 mV (some researchers use 0.2 mV or 0.3 mV) during the ST-segment which endures for at least 30 seconds in consecutive heartbeats (some researchers use from 40 to 60 seconds), correlates positively with myocardial ischemia both in exercise tolerance tests and in ambulatory testing of resting patients and patients performing daily activities. Most patients with stable angina and proven coronary artery disease frequently have episodes of ST-segment depression during daily life. ST-segment changes warm of injury to myocardial tissue even in patients afflicted with otherwise asymptomatic silent myocardial ischemia since they are frequently accompanied by regional disturbances of myocardial perfusion and disturbances of left ventricular function. The monitor analyzes the waveform to determine when the T wave occurs (it should arrive within 400 milliseconds of the R wave) within the current cardiac cycle. After detecting the R wave, the monitor may change the acquisition parameters of the ECG signal (for example, by selecting a different set of impedances in an input amplifier to adjust the bandwidth) to better analyze the waveform structure following the R wave. Referring to FIG. 4, immediately after the comparator detects an R wave, the monitor processes the ECG to measure the leading and trailing R wave slopes, then continues to track the signal down the S wave and back up until the slope diminishes at what is called the J-point. While processing the ECG (in block 320) from the J-point until the waveform crosses the baseline (tested in block 323), the monitor integrates and determines the slope of the signal. If the magnitude (the absolute value) of the integrated signal is larger than at least one predetermined value and remains larger for a consecutive number of cardiac cycles lasting a predetermined time (for example, 40 seconds), then the monitor classifies this event as an ST-segment change. If the integrated signal is below the baseline (a negative signal) and the slope is level or negative, then the monitor classifies the event as ST-segment depression, an indication of ischemia. If the ST-segment is either elevated or depressed by a value greater than a predetermined value (block 325 of FIG. 5) the monitor stores a code in memory to identify this incidence in block 327. If the ST-segment is abnormal, either depressed or elevated, the monitor may use the total duration of deviation persistence as an index of ischemia.

Also in block 320, while processing the ECG following the QRS-complex, the monitor analyzes the data to determine the presence, amplitude, frequency content and duration of the late potential. The presence of late potentials predicts subsequent episodes of ventricular tachycardia, possibly leading to ventricular fibrillation and sudden cardiac death. Late potentials are fluctuations in ECG signal amplitude more than 10 milliseconds after the QRS-complex. The amplitude, frequency content and duration of the late potential are diagnostically significant for predicting the occurrence of ventricular tachycardia and ventricular fibrillation. In an operation distinct from the ST-segment processing, the monitor analyzes the samples beginning about 10 milliseconds following the end of the QRS-complex and persisting for up to 125 milliseconds. In the preferred embodiment of the invention this analysis may include: (1) determining the peak positive and negative deflections of the signal from the baseline amplitude, (2) detecting the presence and duration of the late potential by detecting the first (if any) and last samples wherein the deflection from baseline is greater than a predetermined amplitude within the late potential window, (3) averaging the late potential signal for the present cardiac cycle with that of previous cycles beginning with the first sample having an amplitude greater than the predetermined trigger amplitude, and (4) performing Fourier analysis of the data within the late potential sample window. If the late potential is present and has an amplitude greater than a predetermined level, the monitor logs a code signifying the presence of the late potential as well as the amplitude, duration and one or more parameters specifying frequency content information in block 327 of FIG. 5.

In block 330 the monitor continues to process the ECG to detect the end of the T wave or the occurrence of an R wave (block 333). If the next R wave occurs during the T wave (block 335) the monitor notes this abnormality and stores a code in memory reflecting the incidence of an R-on-T beat in block 337. At the end of the T-wave in block 340 the monitor determines the QT-interval illustrated in FIG. 4. In block 340, the monitor normalizes the QT-interval to cardiac cycle time (R-R) in accordance with standard techniques. In block 343, the monitor compares the normalized QT-interval with a predetermined threshold QT-interval value to detect abnormalities in repolarization. If an abnormality occurs the monitor stores a code to signify the event in block 345.

The monitor may designate a separate circular buffer for each of the precursor events (ventricular arrhythmia, a particular type of ventricular arrhythmia, ST-segment changes, and repolarization) or it may tag each type of precursor with an identifying code and store it in a single circular buffer. Upon the identification of any of the precursors (block 350), the monitor will also update a similar circular buffer memory (block 353) to store the rate of precursor occurrences of any type. If upon updating the precursor rate buffer the monitor detects a rate greater than a predetermined value or otherwise flags a dangerous situation (block 355), the monitor will update a warning memory and may initiate a warning, if danger exists, to an external device in block 357.

As mentioned above, successive samples are stored in block 330. The monitor's storage capacity may be, for example, a number of samples sufficient to characterize a cardiac signal for 30 seconds. The samples may all be transmitted out, in a burst, together with the warning transmitted in block 357. [During real-time monitoring, under the command of the external device, 30 seconds of real-time data samples may be transmitted in a short-term burst every 30 seconds.]

For the implanted AECG monitor to reliably detect precursors of malignant arrhythmias it must acquire high quality electrocardiogram signals. The monitor must maintain signal quality over its intended lifetime (from five to ten years). Consequently, the monitor must resist mechanical and electrical failure, it must reduce and ignore noise from multiple sources, and it must maintain a high quality signal path. An important factor promoting and maintaining signal quality is the implantation of the monitor, the leads and the electrodes. Subcutaneous precordial implantation prevents motion artifact, removes the electrode/skin interface as a source of noise and allows the skin to filter external noise from the signal path.

The implantation method and location are important to maximize signal quality. A physician positions the AECG monitor leads to maximize the ability to analyze the fine detail of interest in electrocardiogram signals. ST-segment change detection is important for diagnosing myocardial ischemia and anticipating sudden death. ST-segment analysis is very sensitive to electrode positioning. Because ST-segment analysis is so important and sensitive to positioning and since placement of electrodes to maximize ST-segment change diagnosis apparently does not compromise the detection of other cardiac events of interest, electrode placement preferably is optimized for the best diagnosis of ST-segment signals.

Figure 6:
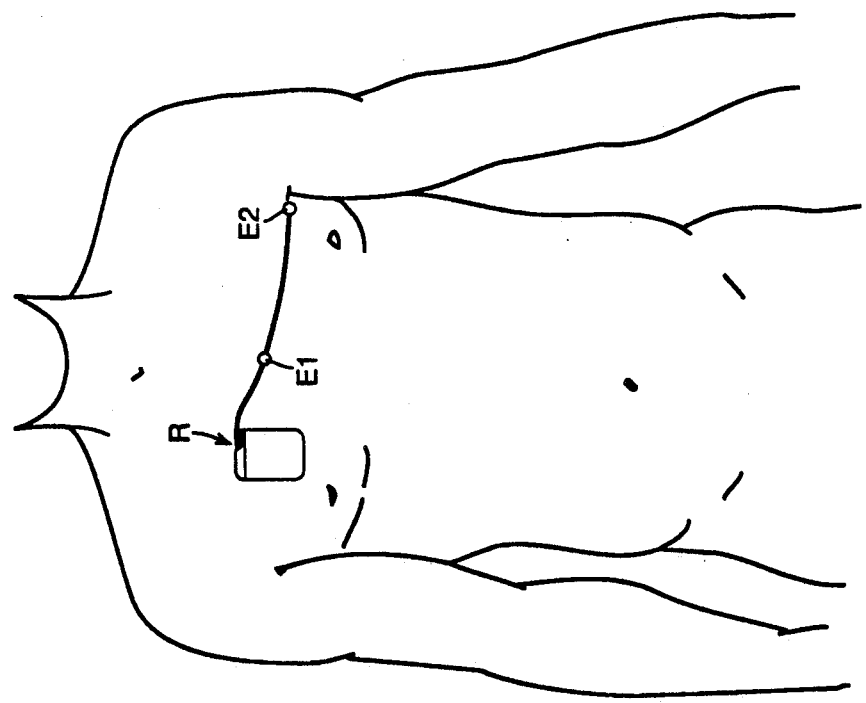
FIG. 6 illustrates an example of the locations at which the implantable electrocardiogram monitor may be implanted.

A single channel or single lead system usually employs three electrodes, two active bipolar leads and a ground. Using subcutaneously implanted electrodes, the separate ground is not necessary, permitting a single bipolar lead system having a total of two electrodes. Most ST-segment analysis using prior art external AECG monitors has been performed using five-electrode, two-bipolar-lead monitors. A single lead system may not be sufficient because, physiologically, it is difficult to position a single lead that will consistently display all ST-segment changes and QRS morphology variation since these events may occur in lead directions to which a single lead is not sensitive. Two leads of AECG data enhance the reliability of the recorded ECG through redundancy, improve the identification and recognition of ectopic cardiac depolarizations, and improve the detection of myocardial ischemia. While either a two- or three-electrode, single-lead monitor or a five-electrode, two-lead monitor is not outside the concept of this invention, the preferred embodiment of the invention uses a three-electrode, dual-lead monitor as illustrated in FIG. 6 with the two leads sharing a common electrode, the case. The lead system of the preferred embodiment balances the need for two electrodes for performing high fidelity signal processing against the desire for less invasion of the body. The three electrodes in this implanted AECG monitor are sufficient for the intended application of this invention because of the high signal quality and the increased reliability of an implanted system. External monitors use multiple leads to serve in a backup capacity in case of mechanical failure or noise on one of the leads. Normally a physician scans the AECG waveforms of the different leads in multi-lead external systems to determine which lead carries the best data, then analyzes that single lead. In the invention, a physician determines the best lead positioning to elicit the desired specific diagnostic information prior to implanting the two leads.

Figure 7:
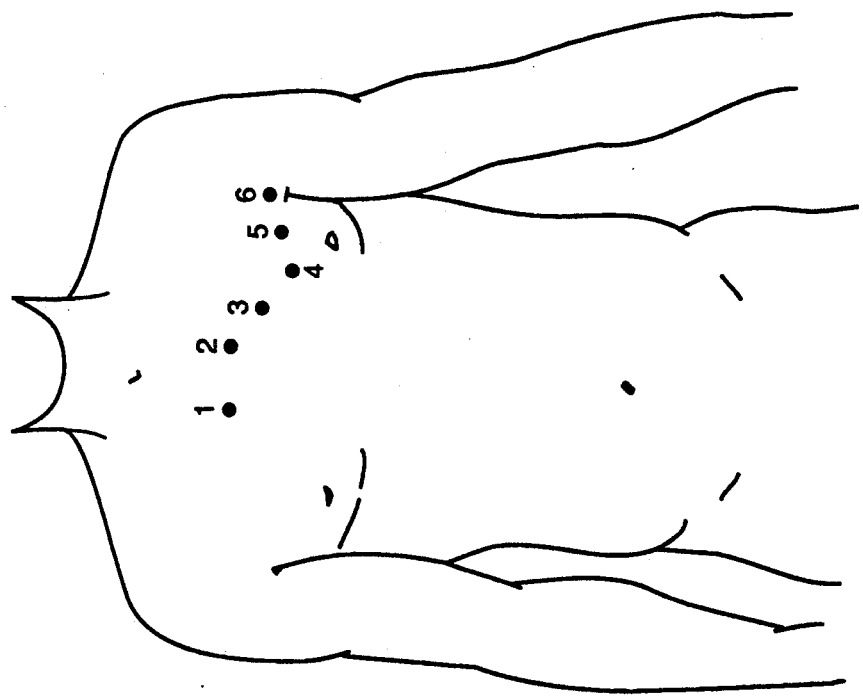
FIG. 7 illustrates the precordial electrode positions traditional in the art of electrocardiography.

In the process of implanting the AECG monitor, the health professional, before implanting either the monitor or its leads, first positions the leads and electrodes by locating the reference electrode (R) in the vicinity of the subclavian pocket (illustrated in FIG. 6—just below the clavicle, wherein the AECG monitor will be implanted) and determining the best locations for the placement of external active electrodes. The procedure for finding the optimum location for the external active electrodes is known in the art of surface ambulatory electrocardiography and includes performing acute ECG testing from all of the six conventional precordial positions shown in FIG. 7, using a standard multi-electrode/multi-lead system, to determine the optimum permanent locations for exploring active electrodes, E1 and E2. A practitioner learned in the art of ECG waveform analysis monitors the signals recorded from each of the standard precordial lead positions for changes in the ST-segment to determine the position, and mark the locations of the bipolar exploring lead or leads (E1 and E2 in FIG. 6), showing the most obvious ischemic changes during exercise tolerance testing. Large deflections in the ST-segment are the indicia for ischemia. The practitioner may adjust the reference and active electrode positions to finely adjust the AECG waveforms to show the greatest ST-segment deflections in exercise tolerance testing.

After finding the best position for the leads, the practitioner implants the case of the implanted AECG monitor subcutaneously within the subclavian pocket described above. The titanium case 400 of FIG. 8A (450 in FIG. 8B) acts as the indifferent electrode for sensing physiological polarizations, including cardiac signals. The physician attaches the proximal end of the lead 405 (455 in FIG. 8B) to the implant using universal connector 410 (460 in FIG. 8B) which forms the adaptation between the lead and the implant, and then closes the tissue around the implant with a suture. The lead 405 forms an electrical connection with either one or two active electrodes (shown as electrodes 415 and 420 in the three electrode system shown in FIG. 8A). FIG. 8B illustrates the monitor using a multiple-ring electrode lead including a tined proximal lead 480 and ring electrodes 465, 470 and 475. The connector holds the lead using a standard pacemaker self-locking mechanism rather than grub screws. The lead is removable. The connector assures reliable electrical contact and is hermetically sealed to avoid leakage.

Figure 9:
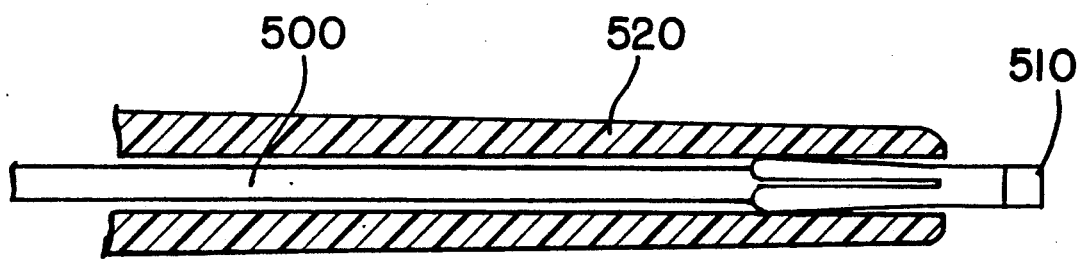
FIG. 9 is an illustration of an introducer used when implanting the lead subcutaneously into the body.

The case serves as the reference or indifferent electrode in the sensing lead system. Using either a tunneling device or a very fine blunt needle, the physician introduces the lead subcutaneously. The introducer 520 shown in FIG. 9 is made of either plastic or stainless steel and coated with Teflon. It has a formable bellows type of construction and an external diameter of less than one millimeter. After implanting the lead 500 using the tunneling procedure and locating the electrodes in the appropriate locations, the practitioner applies pressure to hold the electrode tip 510 with its retracted tines 515 in position and withdraws the introducer. This procedure allows implantation of the lead with a minimum incision at either end.

The lead is the means for sensing cardiac signals and transmitting the signals to the monitor. It is in the form of a very fine helix for maximum fatigue resistance. The lead conducts electrical signals from the electrode to the implant. Like pacemaker leads, implanted AECG monitor leads must be corrosion free and biocompatible. Both types of leads must reliably carry signals for a number of years and resist dislocation over time and withstand conditions of external or internal stresses. The AECG monitor lead is implanted within the subcutaneous layer of tissue and is subject to greater mechanical strains than are cardiac pacemaker leads which, other than at the ends of the lead, can move more freely within a blood vessel. As compared to cardiac pacemaker leads, the AECG monitor leads should have additional strength and a superior ability to withstand mechanical stresses due to flexing, torsion, and elongation. Multifilar leads are multiple intertwined wires and provide the best flexibility and strength. Implantable AECG monitor leads should be optimized for mechanical strength rather than positional stability. The importance of signal quality in the implanted AECG monitor demands low electrical resistance of the leads which is enhanced in multifilar leads. At points along the lead other than at the locations of the electrodes, the conductor is isolated from the body using polyurethane or Silastic insulation. The preferred embodiment of the invention uses leads with polyurethane insulation to provide toughness and higher tensile strength. The diameter of the lead is small (on the order of $2f$ to $3f$).

The physician implants the leads by positioning the electrodes, the electrical connection between the conductor and the tissue, at the marked locations and fixing the leads using a passive fixation to permanently hold the electrode in place. Passive fixation electrodes, which adhere to cardiac tissue by means of a conic shape or tines, are preferred over active fixation electrodes to protect against injury to the tissue. Electrodes should have a large surface area relative to that of cardiac pacemaker leads to enhance sensing of cardiac signals. To reliably measure the fine detail of AECG waveforms, as is required for ST-segment measurements, the signal should have a large ECG amplitude, a high slew rate and minimal interference from extraneous signals. Large surface area electrodes provide the best ECG sensing by decreasing the polarization impedance which attenuates heart signals.

Figure 10:
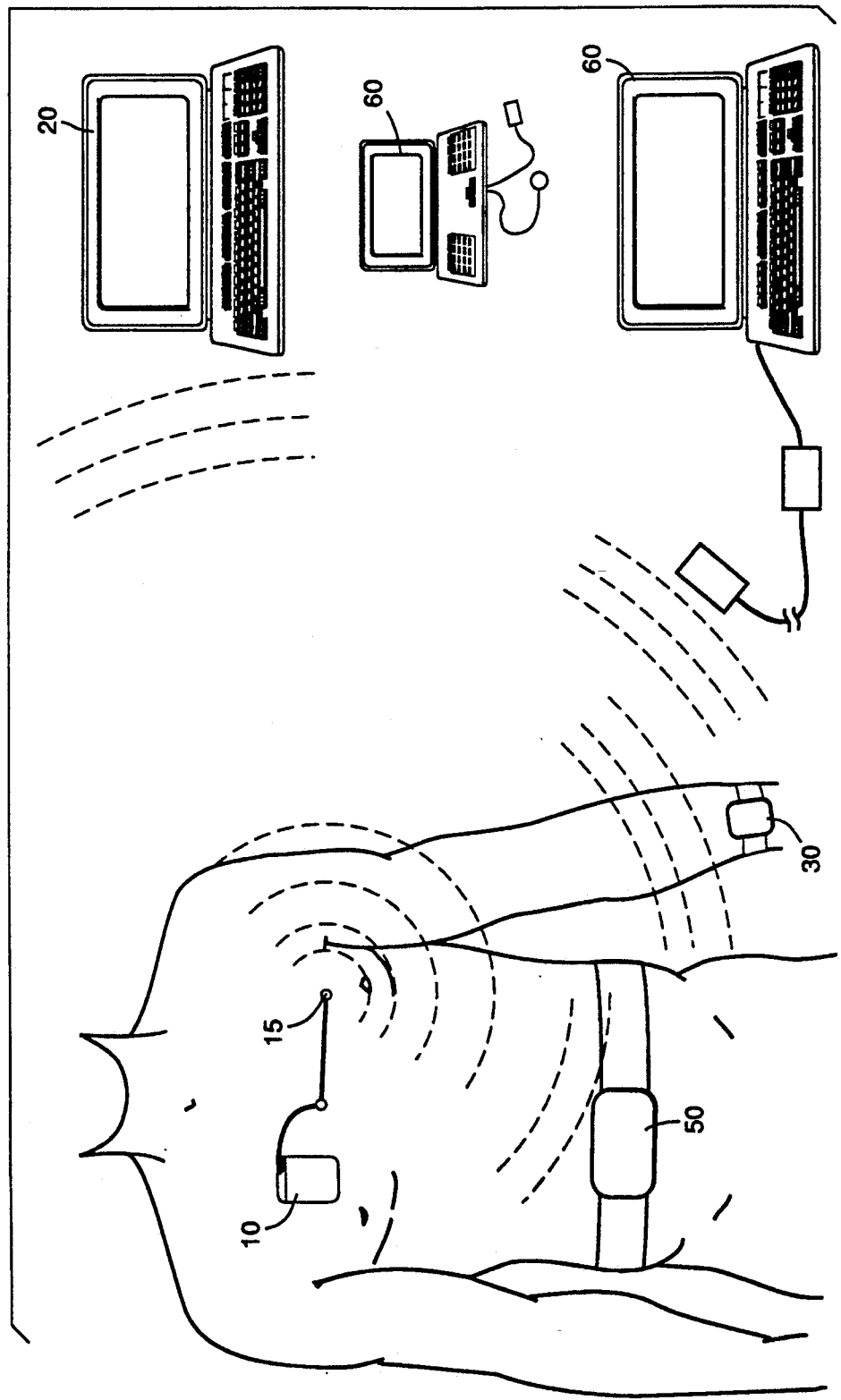
FIG. 10 is an illustration of the telemetric interconnections between the implantable AECG monitor and various external devices.

The implantable AECG monitoring system of the preferred embodiment of the invention includes a number of components. In a particular application, some of the components may not be clinically necessary and are optical. Referring to FIG. 10, system components are the implantable AECG monitor 10 including the transmitter/receiver 15, an external programmer and analyzer 20, a personal communicator alarm device 30, a telephonic communicator 40 which communicates with an external programmer and analyzer 80 in a health care provider's office using modem 70, a full disclosure recorder 50, an external antitachycardia pacemaker or defibrillator 60, and a percutaneous or external drug infusion pump (not shown). The implantable AECG monitor 10 and the external programmer and analyzer 20 are mandatory system components. The need for other components depends on the medical application at hand or objectives of a clinical investigation. All components include at least a telemetry receiver for receiving data and control signals from the implantable AECG monitor 10.

Figure 11:
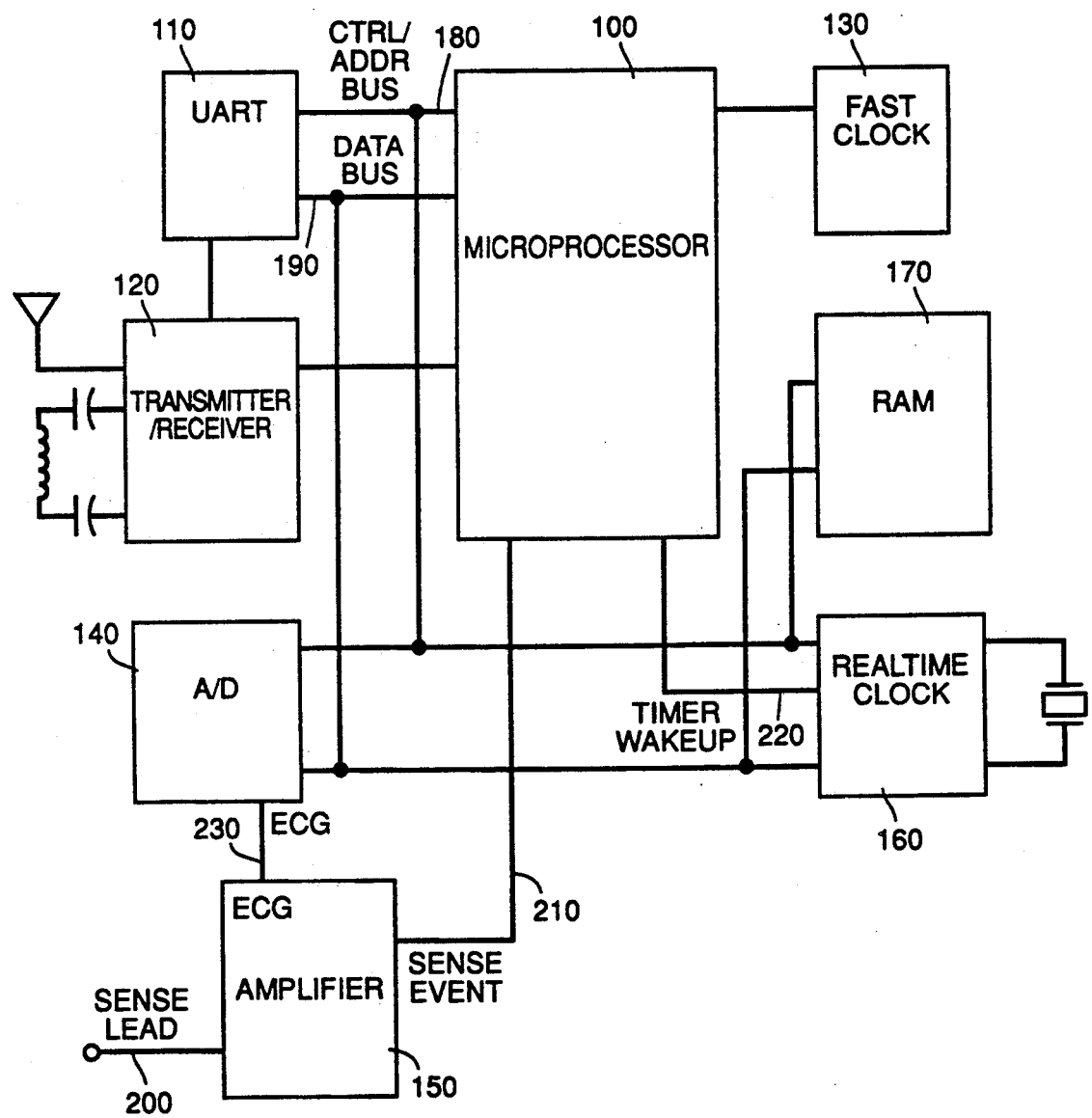
FIG. 11 is a high-level block diagram of the illustrative embodiment of our invention.

FIG. 11 is an illustration in highly symbolic block-diagram form of the implantable AECG monitor. The components of the AECG monitor are optimized for small size and weight, low energy consumption, a long operating life, and high reliability. The implanted AECG monitor receives its energy from a low voltage power source (not shown), nominally a 1AH battery or an equivalent rechargeable cell operating at a voltage ranging from 3.3 to 2.7 volts over the lifetime of the implant.

Microprocessor 100 of FIG. 11, which may be any type of controller, controls the other blocks. In particular, the microprocessor controls the telemetry receiver/transmitter function, memory reading and writing, acquisition of sensed signals, and real-time clock functions to provide the capability of shutting down the entire system when idle. The microprocessor provides standard functionality but also includes a boot ROM, timers, a watchdog timer and an input/output (i/o) port. The watchdog timer is an emergency circuit providing a power-up reset if the microprocessor remains idle for too long a period. The i/o port allows communication between the microprocessor and other circuit elements with no need for extra circuitry outside the microprocessor. The boot ROM configures software in RAM memory to a ready state for power-up operations upon system reset. The fast clock 130 is a high frequency oscillator (for example, 3 MHz) which drives the instruction timing within the microprocessor.

The Microprocessor 100 controls operations of the other circuitry blocks by reading from and writing to the UART 110, the A/D converter 140, the real-time clock 160 and data RAM 170 by means of the control and address bus 180 and the data bus 190. (The control and address bus 180 combines the control and address functions for illustrative purposes only. The control and address lines act independently as is standard in the art of microprocessor communications.) Within the microprocessor there are maskable wakeup circuitry in the form of a data register which enables and disables the ability of the microprocessor to detect wakeup signals from the ECG amplifier 150 (the sense event line 210) and the real-time clock 160 (timer wakeup line 220). Timers within microprocessor 100, the telemetry transmitter/receiver, the ECG amplifier 150 and the real-time clock 160 generate signals which signify pertinent events. The microprocessor determines when and how to respond to these events by means of mask registers which selectively allow the microprocessor to ignore or respond to such events.

One function of the boot ROM software is to control the microprocessor to perform communication with an external device over the telemetry transmitter/receiver on power-up. The device is RAM-based for flexibility and programmability, to allow a variety of program code to operate depending on the desired medical application. The system is designed to readily download program code from the external programmer 20 (FIG. 10) before beginning operation. In response to control signals from the external programmer, the microprocessor downloads program code by receiving encoded program data through the rf transmitter/receiver 120 of FIG. 11, and placing the encoded program data in appropriate locations (defined by the control signals) in program memory located within the random access memory in RAM block 170. The program code residing in memory after the downloading operation governs the operating characteristics of the system and may include a command decoder to process control commands from the external device. A minimum RAM memory size of 64 kilobytes is sufficient to allow programming flexibility to perform different diagnostic and therapeutic functions while retaining a large data storage capacity for storing and analyzing physiological signals.

The telemetry receiver/transmitter performs two-way, digital telemetry to transfer data and programs between the implant and an external device. While performing normal operations the implant will receive from the external programmer and analyzer 20 (FIG. 10) downloaded program object code and other control information to govern data acquisition by the implant. Under the direction of commands from the external programmer and analyzer, the implant will reply with acquired and processed physiological data. It also is a normal operation for the implant to acquire and process the physiological data and from this data analysis to detect warning conditions. In this mode of operation, determined by and under the direction of the downloaded program code, the implant may initiate communication with an external device to warn of abnormal physiological conditions. (The implant may also warn the external device of a malfunction within the implanted AECG monitor in response to an attempt and failure of a self-diagnostic test.) The telemetry receiver/transmitter 120 is made up of the rf transmitter, the rf receiver, and the UART 110 which directs data flow from the rf circuits to the data bus under the control of the microprocessor 100. The implantable AECG monitor transmits information to an external device with a range of at least 20 feet at a telemetric data transmission frequency of 40 to 200 Mhz. The rf receiver operates at the telemetric frequency on the order of about 2 MHz. UART 110 controls data communications in response to input/output commands from microprocessor 100 which configure the UART to perform reception or transmission. It includes a standard serial interface, a data buffer, and circuitry for error detection coding and decoding.

When the telemetry transmitter/receiver is idle, the microprocessor disconnects power to the communication circuitry. In one intended mode of operation the microprocessor 100 may detect a predetermined physiological or operational condition while analyzing data or performing self-diagnostics which will trigger communication with a nearby external device. Upon detecting this condition the microprocessor will transmit a beacon signal to the external device. The beacon signal informs the device that the implantable AECG monitor will change its communication mode from transmission to reception and listen for control information for a short time window following the beacon. For example, an idling microprocessor may send beacon signals every five seconds to allow communication to begin within a 2 millisecond window.

In a clinical environment, more than one patient may have monitoring systems, each with an implantable monitor and an external communication device. The monitoring system must have a means for arbitrating communications so that the implantable device will interact with its corresponding device receiver (the implant and receiver pair for the same patient). The implantable monitor and the external device arbitrate communications using handshake techniques which are standard in the art of communications. For example, the preferred embodiment of the invention uses a response delay procedure, as illustrated in the flow chart of FIG. 14, for the implant to identify itself to the external device. When the implant detects a warning condition in block 700, it sends the beacon signal to the external device (block 705). The external device, which is idling in wait state 750, detects the beacon signal in block 755 and responds by sending a synchronization sequence to the implant (block 760). The external device has programming which identifies and corresponds to the serial number of the implant. The implant receives the synchronization sequence (block 710), then waits a delay interval (block 715) keyed to one or more digits of its serial number before responding in block 720. The external device times the interval from the end of the initialization sequence to its reception of the response from the implant in block 765 and determines whether the time of the delay is appropriate for the appropriate digit or digits in the programmed serial number (block 770). If the delay does not correspond to the correct serial number (tested in logic block 775), the communication is not sustained (block 780). Otherwise, the implant and the external device either loop back to process more digits of the serial number (logic is determined in blocks 725 and 785 for the respective devices, branching to 715 and 765). If all digits of the serial number have been correctly transmitted and received, the communication link between devices is established and telemetry proceeds (block 730 in the implantable monitor sends the data and block 790 of the external device receives the data). In this manner, the external device and the implant communicate all serial number digits at once or each digit of the serial number separately with synchronization pulses separating and defining each digit. If there is no external device programmed to receive data from an implant with the corresponding serial number in the vicinity of the implant, the implant will attempt to send its data without establishing communication with any device.

The microprocessor 100 controls device operations using control signals written to the real-time clock 160. One control code is a prescaler value which determines the time scaling of wake-up events. Typical prescaler values will set the timer to increment or decrement in steps ranging in duration from 1 to 8 milliseconds. A second type of control signal is the time value which the microprocessor loads into the real-time clock to begin timing an interval. When the real-time clock counts up to the count value or down to zero, the real-time clock issues a wake-up signal on line 220. Upon receiving the wake-up signal, the microprocessor uses an arbitration scheme as is known in the art of computers to determine which input signal requested the wakeup. The microprocessor services the wakeup, sets the timer for the next desired interval, and then resets the wake-up signal to prepare for the next timed event. The prescaler and timer encoded signals determine the duration of inactivity. The microprocessor controls the real-time clock 160 to time telemetry beacon intervals, ECG sampling, miscellaneous updating, and to time other functions depending on the programmed medical application.

Under the control of the microprocessor 100, the implantable AECG monitor senses electrocardiographic signals from the sense lead 200 which is in electrical contact with the electrode. The signals on the sense lead first proceed to the ECG amplifier for initial filtering and processing. The ECG amplifier 150 includes a standard true instrumentation amplifier with a programmable bandwidth, allowing the microprocessor to tailor the signal filtering parameters to a particular type of electrocardiogram features as may be required to perform a desired task. (A true instrumentation amplifier characteristically has a high input impedance, full differential amplifiers on the input and output, high gain, and an adjustable input resistance.) For example, bandwidth requirements vary when performing diverse operations such as measuring ST-segment changes, monitoring heart rate and acquiring high quality electrocardiograms. The true instrumentation amplifier produces the high quality signal necessary for detailed electrocardiogram analysis by filtering input noise and providing minimal phase and baseline shift and a flat amplitude versus frequency response in the selected bandwidth. The wide range of bandwidths allows flexibility in the selection of analysis methods. The programmable bandwidth of the ECG amplifier 150 for reproducing high quality electrocardiograms ranges from the heart rate frequency (commonly 0.5 to 5 Hz) to 100 times the heart rate (about 500 Hz). When the microprocessor sets the bandwidth in preparation for ST-segment analysis, it selects a much lower frequency range (0.01 Hz to 30 Hz).

In addition to the standard true instrumentation amplifier, the ECG amplifier 150 circuit includes a comparator with a programmable threshold for generating wake-up signals to the microprocessor over the sense event wake-up line 210. The microprocessor may program the threshold circuitry to generate wake-up signals upon the detection of either a programmed signal amplitude or the derivative of the amplitude (to detect amplitude changes). The monitor generally uses the comparator to detect ECG features such as the R-wave. The monitor preferably detects R-waves by programming the threshold circuitry to generate wake-ups when the derivative of the ECG signal is greater than a particular value as selected by the physician or automatically in a manner known in the art of cardiac pacemakers. (A common threshold, also called sensitivity, value is 1 m V/msec). To reduce the energy consumption of the implantable device, the monitor may use the thresholding feature to disable ECG sampling except when the signal contains features of interest. For example, the monitor may discontinue sampling operations following the analysis of a QRST-complex and set the comparator to detect the next R-wave. Upon the occurrence of the next R-wave, the comparator will wake up the microprocessor and allow it to direct operations to begin sampling the QRST data for the current cardiac cycle. (The monitor would not use this mode of operation when signals of interest are contained in the signal previous to the R-wave. In many cases the monitor may measure QT-interval by timing the signal from the R-wave to the T-wave and assuming a constant time interval from the Q-wave to the R-wave. This is allowable to conserve energy because the QR-interval is nearly constant, even in abnormal hearts.)

Data from the ECG amplifier 150 is converted from analog to digital form by analog to digital conversion circuitry 140. The ECG amplifier circuitry includes an anti-aliasing filter to minimize the artifact caused by digitization of the signal. Programming within the microprocessor controls the conversion rate within the range from 64 to 1000 samples per second. Programming of the microprocessor also directs the digital output of the ECG amplifier to one or more destinations (to the rf transmitter to allow transmission of raw data, to memory 170 or 180, or to the microprocessor itself for data storage and analysis). Data acquisition control by the microprocessor allows the implanted AECG monitor to constantly analyze data and, in response to that analysis, to perform intelligent data acquisition. For example, the monitor may increase the sample rate or amplifier bandwidth or begin sampling after a pause in response to a particular sensed event.

The above discussion indicates how the implanted nature of the AECG monitor and the implantation procedure maximize ECG signal quality. Another factor assuring signal quality is the absence of cumulative distortion between the various system components. In the preferred embodiment of the invention, all stored and transmitted signals and information are converted to digital form early in the signal path and maintained in digital form to assure signal quality. No phase distortion is introduced as is the case in external AECG systems. The high quality instrumentation amplifier of block 150 in the signal acquisition circuitry of the implanted monitor has its bandwidth programmed to produce the optimum signal according to the ECG parameter currently of interest. The signal from the instrumentation amplifier is then immediately digitized in block 140 for analysis and storage.

The system can also be programmed to operate in a "look-back" mode to provide for the study of precursors to a triggering event wherein digital conversion circuitry 140 constantly digitizes ECG data for periods on the order of seconds while the microprocessor stores the data in a circular memory. Upon the occurrence of a predetermined triggering event the microprocessor discontinues circular memory updating and retains the last samples before the triggering event, allowing important data to remain unchanged either for internal analysis using the microprocessor or for transmission using telemetry upon external activation.

Again referring to FIG. 10, the second essential component of the AECG monitoring system is the external programmer and analyzer 20. This device is similar to recorders for communicating with external AECG monitors and programmers for interacting with cardiac pacemakers. The external programmer and analyzer 20 may be essentially a computer system with added functionality provided by a telemetry interface wand. The wand includes rf transmission and reception circuitry similar to that in the implantable AECG monitor 10. The telemetry interface wand receives the signals sent by the implantable AECG monitor 10. Software in the external programmer and analyzer is configured to provide a human interface for controlling the operations performed by the implantable AECG monitor. In response to commands of the operator, the programmer analyzer reads and displays data from the monitor, transmits control parameters to the monitor, and downloads diagnostic and application routine machine code from a program library into the RAM memory of the AECG monitor.

The external programmer and analyzer controls the implantable device by sending control signals at a maximum rate of a few commands per second to direct its operations. The implantable AECG monitor transmits application-specific data, for example electrocardiograms, to the external device for display and analysis. The external programmer and analyzer may use the data telemetered from the implant according to the specifications of a diagnostic or therapeutic protocol to determine what command to send to the implant and when to send it.

The personal communicator alarm 30 acts as the human interface between the implantable AECG monitor 10 and the patient. The alarm responds to application-dependent messages from the monitor. Programs loaded from the external programmer and analyzer into the implantable device include message output routines which are triggered by physiological or diagnostic events sensed by the monitor. Electronic components of the personal communicator and alarm 30 are a subset of those comprising the external programmer and analyzer. These components may include a microprocessor, communication circuitry, and an audio or visual alarm signal for notifying the patient of triggering events. The telemetry receiver within the personal communicator alarm 30 is similar to and compatible with that of the implantable AECG monitor. The implantable AECG monitor sends message codes to the alarm, causing the alarm to respond by activating a light emitting diode or audio alarm. In this manner the monitor warns the patient to take medication or otherwise seek medical intervention.

In addition to its function as a warning device in response to alarm signals from the implantable AECG monitor 10, the personal communicator alarm 30 may be used as a control device to activate certain control functions within the implantable AECG monitor 10. For example, a physician wanting to view the electrical manifestation of a patient symptom may direct the patient to activate the personal communicator alarm 30 upon feeling the physical effects of the symptom. Similarly, the patient may set a timer in the personal communicator to activate telemetry at a particular time of day or night to allow analysis of physiological data sampled when the patient is in a particular state (sleeping, for example). The personal communicator alarm 30 sends a command to the implantable AECG monitor 10 requesting the transmission of stored physiological event precursors or other signal information including unprocessed signal samples. The implantable AECG monitor may send the information to a third device such as an external programmer and analyzer 20, a telephonic communicator 40 or full disclosure recorder 50.

The telephonic communicator 40 is another device for responding to messages from the implantable AECG monitor 10. Programs loaded from the external programmer and analyzer 20 into the implantable monitor determine the physiological and diagnostic events to which the monitor will respond by activating the telephonic communicator. The electronic components of the telephonic communicator are a subset of those comprising the external programmer and analyzer including a microprocessor and circuitry for receiving messages from the implantable AECG monitor and sending messages over telephone lines. The telemetry receiver within the telephonic communicator 40 receives data in a manner similar to and compatible with that of the implantable AECG monitor. Event codes from the implantable unit cause the telephonic communicator 40 to establish a telephonic communication link with a previously designated physician or clinic. The telephonic communicator accesses a telephone number according to the directions provided by either the implanted AECG monitor or the programming within the telephonic communicator itself. The telephonic communicator, like the implantable AECG monitor, is programmable by the external programmer and analyzer 20. Upon accessing the designated physician or clinic, the telephonic communicator sends data and personal and diagnostic information supplied by the implantable AECG monitor.

Another optional component of the AECG monitoring system is the full disclosure recorder 50 of FIG. 10 for allowing visual inspection and analysis of the AECG recordings. In addition to a microprocessor and communication circuitry the full disclosure recorder may have additional memory for storing large amounts of data in the form of semiconductor RAM, magnetic disks, magnetic tapes, or any other mass storage memory means. The microprocessor may perform data compression and reduction routines to store data more efficiently.

The implantable AECG monitor 10 and the full disclosure recorder 50 communicate in a burst mode to conserve energy. The implantable AECG monitor compresses and stores data until its memory (for example, 64 Kbytes) is full. Storage time is on the order of ten minutes. When the memory is full, the implantable AECG monitor sends a control signal to the full disclosure recorder to signal the beginning of data transmission. The implanted monitor sends the accummulated data to the recorder in a burst mode lasting on the order of five seconds. Burst mode transmission allows data transmission of large quantities of data using the lowest energy possible per bit.

The implantable AECG monitor 10 can control therapeutic devices including antitachycardia pacemakers and defibrillators 60, and drug infusion pumps. These devices are known in the art and adapted to this invention by the addition of a telemetry receiver and transmitter similar to and compatible with that of the implanted AECG monitor. When the AECG monitor detects a triggering event, it sends control signals by telemetry to an implanted defibrillator or infusion pump.

Figure 12:
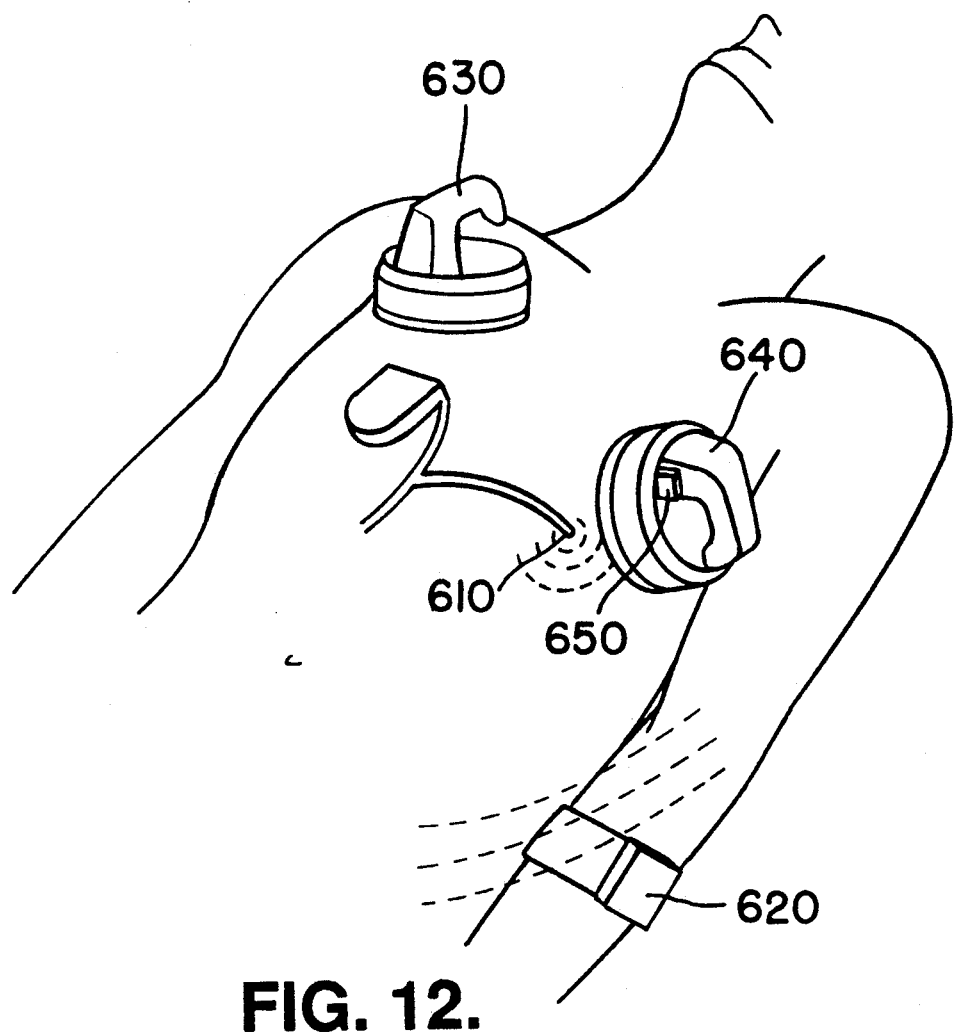
FIG. 12 illustrates the method of operation of the implanted AECG monitor in conjunction with a personal communicator alarm and an external defibrillator in the precordial electrode positions traditional in the art of defibrillation.

In many cases a patient will have an implanted or external antitachycardia pacemaker and defibrillator or a drug infusion pump. Referring to FIG. 12, the implantable AECG monitor 600 sends signals to the personal communicator alarm 620 to notify the patient of the occurrence of a triggering event. The message sent by the monitor may, for example, be a code requesting attachment of an external defibrillator. The personal communicator alarm notifies and prompts the patient or an attendant to attach external defibrillator paddles 630 and 640, or another therapeutic device to the chest. In a clinical setting, more than one cardiac patient may have an implantable AECG monitor and its associated therapeutic device. The arbitration method discussed previously illustrates how the implantable monitor interacts with the correct personal communicator alarm. A second arbitration scheme is necessary to assure that the monitor interacts with a therapeutic device attached to the same patient. After the patient attaches the therapeutic device, it may inject low level current pulses into the body for the purpose of establishing communication with the implantable AECG monitor using the body as a conductive link. If the therapeutic device is a defibrillator, for example, it will inject current pulses across the paddles. Referring to FIG. 13, the current pulses transmitted by the defibrillator will be superimposed on the electrocardiogram signals of the heart. The current pulses from the therapeutic device are in the form of a timed code or signature which establish that the device and the monitor are connected to the same patient. The implantable AECG monitor detects and decodes the information as pulses within the electrocardiogram. After establishing the communication link in this manner, the implantable monitor will respond to the device over the telemetry link. The therapeutic device must include the telemetry receiver 650 of the aforementioned external devices. The communication between the implantable AECG monitor and the therapeutic device directs the external device to discharge at the appropriate time and in the correct manner.

Although the invention is described with reference to a particular embodiment, it is to be understood that this embodiment is merely illustrative of the application of the principles of the invention. Numerous modifications may be made therein and other arrangements may be devised without departing from the spirit and the scope of the invention.

We claim:

1. A chronically and totally implanted heartbeat signal monitor capable of communicating with a message-receiving device, comprising:
    subcutaneous sensing means, adapted to be located remote from a patient's heart, for sensing heartbeat signals,
    means responsive to sensed heartbeat signals for determining a heart abnormality, and
    means responsive to said determining means for communicating with said message-receiving device to report on a heart abnormality.

2. A chronically and totally implanted heartbeat signal monitor in accordance with claim 1 wherein said communicating means initiates a communication independent of the operation of said message-receiving device.

3. A chronically and totally implanted heartbeat signal monitor in accordance with claim 2 wherein said communicating means reports a heart abnormality in the form of a diagnostic message.

4. A chronically and totally implanted heartbeat signal monitor in accordance with claim 1 wherein said sensing means is adapted for implantation at a location at which the sensed heartbeat signal is comparable to a standard body surface electrocardiogram signal.

5. A chronically and totally implanted heartbeat signal monitor in accordance with claim 1 wherein said communicating means is further operative to transmit heartbeat signal samples to said message-receiving device to allow heartbeat signal reconstruction.

6. A chronically and totally implanted heartbeat signal monitor in accordance with claim 5 wherein said communicating means transmits said heartbeat signal samples in a burst mode.

7. A chronically and totally implanted heartbeat signal monitor in accordance with claim 1 wherein said determining means applies to sensed heartbeat signals standard body surface ambulatory electrocardiography diagnostic criteria for determining heartbeat abnormalities.

8. A chronically and totally implanted heartbeat signal monitor in accordance with claim 1, wherein said monitor is capable of communicating with an external therapy applying device, and further including means for exchanging information in accordance with an established protocol with said external therapy applying device, said information exchanging means being operative to insure that said external therapy applying device applies therapy to the patient requiring it and in whom the signal monitor is implanted.

9. A chronically and totally implanted heartbeat signal monitor in accordance with claim 8 wherein said information exchanging means is operative to sense predetermined electrical signals applied directly to the patient by said external therapy applying device and in response thereto to control said device to apply its therapy.

10. A chronically and totally implanted heartbeat signal monitor in accordance with claim 1 wherein said sensing, determining and communicating means all operate continuously, independently of external control.

11. A chronically and totally implanted heartbeat signal monitor in accordance with claim 10 wherein the monitor is adapted to remain implanted in a patient for a time interval measured in years.

12. A chronically and totally implanted heartbeat signal monitor in accordance with claim 1 wherein said sensing means include electrodes adapted for implantation beneath the skin of a patient at precordial positions which are standard in body surface ambulatory electrocardiography.

13. A chronically and totally implanted heartbeat signal monitor in accordance with claim 1 wherein said sensing means includes at least two electrodes, and said determining means is further operative to measure, and said communicating means is further operative to report on, the impedance between said at least two electrodes.

14. A chronically and totally implanted heartbeat signal monitor in accordance with claim 1 wherein said communicating means further reports heart activity information along with the times at which said activity occurred to allow external analysis of the effect of drugs on the patient.

15. A chronically and totally implanted heartbeat signal monitor in accordance with claim 1 further including means responsive to externally generated and transmitted signals for accepting downloaded signal acquisition and analysis programs to allow tailoring of the monitor to the needs of a particular patient.

16. A chronically and totally implanted heartbeat signal monitor in accordance with claim 1 wherein said determining means is operative to distinguish between normal cardiac rhythms and arrhythmias by setting an arrhythmia rate threshold at a higher level when the patient is exercising.

17. A chronically and totally implanted heartbeat signal monitor in accordance with claim 1 whose life is extended by the omission of a pacing capability.

18. A chronically and totally implanted heartbeat signal monitor in accordance with claim 1 wherein said determining means adjusts the bandwidth which characterizes the processing of the sensed heartbeat signals in accordance with the particular part of a cardiac cycle which is in progress.

19. A chronically and totally implanted heartbeat signal monitor in accordance with claim 1 wherein said sensing means includes electrodes adapted to be positioned for optimizing ST-segment analysis.

20. A chronically and totally implanted heartbeat signal monitor in accordance with claim 1 wherein said communicating means further alerts the patient to commence self-treatment.

21. A chronically and totally implanted heartbeat signal monitor capable of communicating with a message-receiving device, comprising:
   subcutaneous sensing means for sensing heartbeat signals remote from a patient's heart, said sensing means including electrodes adapted for implantation beneath the skin of a patient at precordial positions which are standard in body surface ambulatory electrocardiography,
   means responsive to sensed heartbeat signals for deriving cardiac information therefrom, and
   means responsive to said deriving means for communicating with said message-receiving device to report on the derived cardiac information.

22. A method for monitoring heartbeat signals comprising the steps of:
   chronically and totally implanting a heartbeat signal monitor having an electronic device and at least one sensing lead, said sensing lead having an electrode thereon, and said electronic device being capable of deriving cardiac information from signals appearing at said electrode and telemetering such information to an external device, and
   implanting said at least one sensing lead subcutaneously with said electrode being positioned beneath the skin of the patient, remote from the patient's heart, at a precordial position which is standard in ambulatory electrocardiography.

23. A method for monitoring heartbeat signals by a heartbeat monitoring device comprising the steps of:
   sensing heartbeat signals from at least one electrode, positioned beneath the skin of the patient and remote from the patient's heart, at a precordial position which is standard in ambulatory electrocardiography,
   analyzing sensed heartbeat signals to detect a morphology and timing indicative of a heart abnormality,
   upon the detection of a heart abnormality, initiating communication with a non-implanted message-receiving device independent of the operation of said message-receiving device,
   identifying the non-implanted message-receiving device adapted to communicate with the heartbeat monitoring device, and
   transmitting diagnostic messages to said message-receiving device upon successful device identification.

24. A method for monitoring heartbeat signals in accordance with claim 23 wherein the step of transmitting diagnostic messages is performed in a burst mode.

25. A method for monitoring heartbeat signals in accordance with claim 23 further including the steps of:
   exchanging information in accordance with an established protocol with an external therapy applying device, said information exchanging step being operative to insure that said external therapy applying device applies therapy to the patient requiring it and in whom the signal monitor is implanted.

26. A method for monitoring heartbeat signals in accordance with claim 25 wherein said information exchanging step includes the sub-steps of sensing predetermined electrical signals applied directly to the patient by said external therapy applying device and in response thereto controlling said device to apply its therapy.

27. A method for monitoring heartbeat signals in accordance with claim 23 further including the steps of:
sensing the impedance between at least two implanted electrodes, and
analyzing the sensed impedance together with the sensed heartbeat signal to detect a morphology and timing indicative of a heart abnormality.

28. A method for monitoring heartbeat signals in accordance with claim 23 wherein said diagnostic message transmitting step alerts the patient to commence self-treatment.

* * * * *